United States Patent [19]

Prasad et al.

[11] 4,081,447
[45] Mar. 28, 1978

[54] 5-[2-HYDROXY-3-(3,4-DIMETHOXY PHENETHYLAMINO)]-PROPOXY-3,4-DIHYDRO CARBOSTYRIL AND PHARMACEUTICALLY ACCEPTABLE SALTS THEREOF

[75] Inventors: Raj Nandan Prasad, Pierrefonds, Canada; Herman Hal Stein, Skokie, Ill.; Karin Rosemarie Tietje, Philipsburg, Canada

[73] Assignee: Abbott Laboratories, North Chicago, Ill.

[21] Appl. No.: 566,600

[22] Filed: Apr. 9, 1975

[51] Int. Cl.² .................... C07D 215/22; A61K 31/47
[52] U.S. Cl. ........................... 260/288 R; 210/287 K; 424/288
[58] Field of Search ......... 260/288 R, 288 CE, 287 K

[56] References Cited

U.S. PATENT DOCUMENTS

| | | | |
|---|---|---|---|
| 3,340,266 | 9/1967 | Howe et al. | 260/288 R |
| 3,910,924 | 10/1975 | Tamura et al. | 260/288 R |

FOREIGN PATENT DOCUMENTS

| | | | |
|---|---|---|---|
| 6,408,650 | 2/1965 | Netherlands | 260/288 R |
| 1,344,976 | 1/1974 | United Kingdom | 260/288 R |
| 1,058,822 | 2/1967 | United Kingdom | 260/288 R |

OTHER PUBLICATIONS

Nakagawa et al.; Chem. Abs., vol. 82:156122v and 156123w, (1975).
Nakagawa et al.; Chem. Abs., vol. 80:82715a, (abstract of Ger. Offen. 2,302,027), (1974).
Nakagawa; Chem. Abs., vol. 81:72672r; 91375n.
Nakagawa et al.; Chem. Abs., vol. 82:139972e, 139974g, 125293x, (1975).

*Primary Examiner*—Donald G. Daus
*Assistant Examiner*—Mary Vaughn

*Attorney, Agent, or Firm*—Vincent A. Mallare; Robert L. Niblack

[57] ABSTRACT

A group of β-blockers represented by the formula

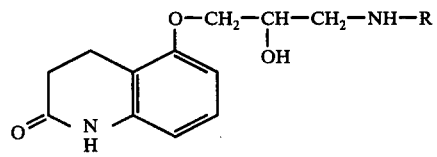

wherein R is

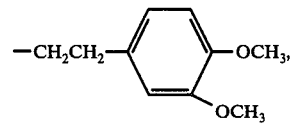

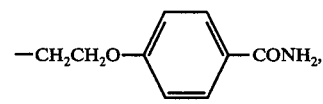

or

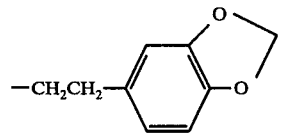

and the physiologically compatible acid addition salts thereof.

These β-blockers are β-adrenergic receptor blocking agents which are useful in the treatment of angina pectoris, heart arrhythmia, and high blood pressure.

2 Claims, No Drawings

5-[2-HYDROXY-3-(3,4-DIMETHOXY PHENETHYLAMINO)]-PROPOXY-3,4-DIHYDRO CARBOSTYRIL AND PHARMACEUTICALLY ACCEPTABLE SALTS THEREOF

BACKGROUND OF THE INVENTION

This invention relates to novel β-blockers, and more particularly relates to β-adrenergic blocking agents which are useful in the treatment of prophylaxis of angina pectoris, heart arrhythmia and high blood pressure.

β-Adrenergic blocking agents represent a class of cardiac arrhythmias and angina pectoris, a disease characterized by an insufficient myocardial oxygen supply in the face of a greater oxygen demand. The increased demand for oxygen during exercise is triggered by the adrenergic β-receptor stimulants, epinephrine and norepinephrine. Likewise, many arrhythmias during or following myocardial infraction are produced by the same adrenergic amines. Blockade of the β-adrenergic stimulants by β-adrenergic blocking drugs relieves many types of arrhythmias and reduces the demand for oxygen by the heart, thereby producing striking pain relief and increased exercise tolerance in angina pectoris.

DETAILED DESCRIPTION OF THE INVENTION

The β-blocking agents of the present invention are provided by compounds represented by the following formula

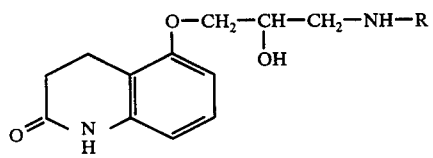

wherein R is

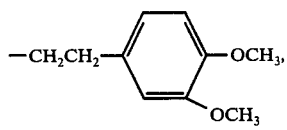

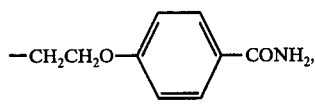

or

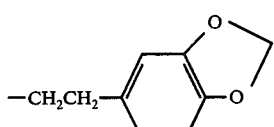

and the physiologically compatible acid addition salts thereof. The compounds of this invention contain asymmeteric carbon atoms and may thus exist in the form of optically active isomers as well as racemic mixtures.

The compounds which have been found to be effective β-blockers include:

5-[2-hydroxy-3-(3,4-dimethoxy phenethylamino)]-propoxy-3,4-dihydrocarbostyril;

5-[2-hydroxy-3-(4-carbamyl phenoxyethylamino)]-propoxy-3,4-dihydrocarbostyril; and 5-[-2-hydroxy-3-(3,4-methylenedioxy-phenethylamino)]-propoxy-3,4-dihydrocarbostyril.

The compound, 5-[2-hydroxy-3-(3,4-dimethoxy phenethylamino)]-propoxy-3,4-dihydrocarbostyril has also been found to be cardioselective.

The compounds of the present invention can generally be prepared by reacting the corresponding amine with 5-(2,3-epoxy)propoxy-3,4-dihydrocarbostyril. For example, the compound, 5-[2-hydroxy-3-(3,4-dimethoxy phenethylamino)]-propoxy-3,4-dihydrocarbostyril is prepared as illustrated in the following reaction scheme:

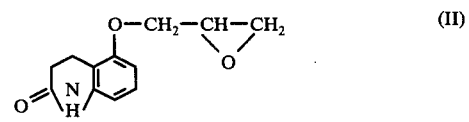

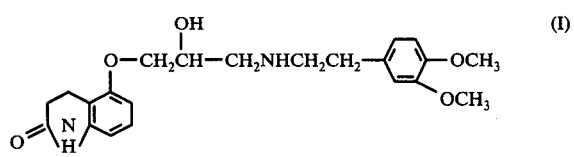

As shown in the above reaction scheme, the compound 5-[2-hydroxy-3-(3,4-dimethoxy phenethylamino)]-propoxy-3,4-dihydrocarbostyril (I), is prepared by reacting 3,4-dimethoxy phenethylamine and 5-(2,3-epoxy)-propoxy-3,4-dihydrocarbostyril.

The epoxide is prepared by the reaction of 5-hydroxy-3,4-dihydrocarbostyril (Y. Tamura et al, *Chem. Ind.*, 1435 (1970) and epichlorohydrin in DMF in the presence of NaH. This method gives a better quality of the epoxide than described by K. Nakagawa et al, in the *Journal of Medicinal Chemistry*, 17, 529 (1974). 3,4-Dimethoxyphenethylamine is commercially available.

4-(2-Amino-ethoxy) benzamide can be prepared by the use of one of the following methods, using standard synthetic techniques from commercially available starting materials.

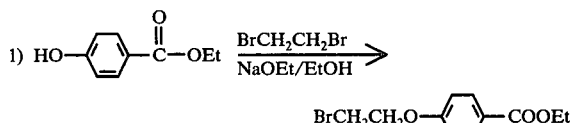

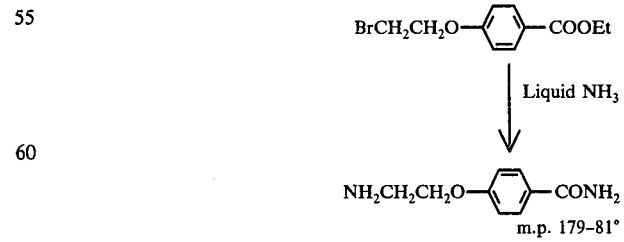

m.p. 179–81°

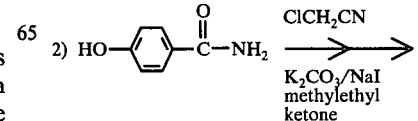

-continued

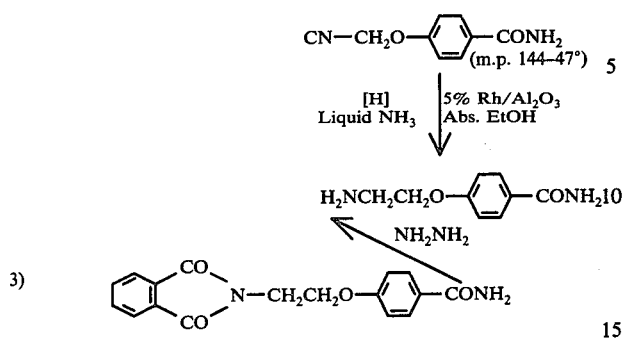

In order to illustrate the synthesis and pharmacological activity of the new drugs, reference is made to the following examples. These examples are not to be construed as the only preparatory procedures and are not intended to limit the invention in any respect.

EXAMPLE I

Preparation of 5-[2-Hydroxy-3-(3,4-Dimethoxy Phenethylamino)]-Propoxy-3,4-Dihydrocarbostyril A mixture of freshly distilled 3,4-dimethoxy phenethylamine (1.27 g.; 0.007 mole) and 5-(2,3-epoxy)-propoxy-3,4-dihydrocarbostyril (1.5 g.; 0.0068 mole); [K. Nakagawa et al, *J. Med. Chem.*, 17, 529 (1974)] in methanol (35 ml.) was refluxed for 3 hours. The solvent was evaporated. The residual oil was triturated with absolute ethanol-ether and filtered from some impurities. The filtrate was acidified with ethereal HCl. The gummy hydrocholoride was separated, dissolved in water and extracted with ethyl acetate. The aqueous layer was evaporated to dryness under reduced pressure. The residue was recrystallized from absolute ethanol to give the analytical sample melting at 177°–180°; $R_f$ 0.58 (methanol/CHCl$_3$, 1:9).

Analysis Calcd. for: $C_{22}H_{28}N_2O_5$·HCl; Requires: C, 60.48; H, 6.69; Cl, 8.11; N, 6.41. Found: C, 60.10; H, 6.92; Cl, 8.52; N, 6.17.

EXAMPLE II

5-[2-Hydroxy-3-(4-Carbamoyl Phenoxyethylamino)]-Propoxy-3,4-Dihydrocarbostyril

A mixture of 4(2-aminoethoxy) benzamide (0.5 g.; 0.0028 mole) and 5-(2,3-epoxy) propoxy-3,4-dihydrocarbostyril (0.52 g.; 0.0024 mole) in absolute ethanol (25 ml.) was refluxed for 72 hours. The mixture was filtered hot and the residue (0.8 g.; m.p. 180°–184°) containing a dimer was purified by preparative TLC to give 406 mg. of the pure product melting at 207°–209°; $R_f$ 0.57 (methanol/chloroform; 3:7).

Analysis Calcd. for $C_{21}H_{25}N_3O_5$: C, 63.14; H, 6.31; N, 10.52. Found: C, 62.62; H, 6.39; N, 10.34.

Nmr and mass spectra confirmed the structure.

The required 4-(2-aminoethoxy) benzamide was prepared by heating 4-(2-bromoethoxy) benzoic acid, ethyl ester (45.0 g.) with liquid ammonia (250 ml.) at 100°–120° in an autoclave for 8–10 hours. This reaction gave A. 4-(2-Aminoethoxy) benzoic acid, ethyl ester hydrobromide (m.p. 193°–195° from acetone; $R_f$ 0.63; methanol/chloroform, 3:7).

Analysis Calcd. for $C_{11}H_{15}NO_3$·HBr: C, 45.53; H, 5.56; N, 4.83. Found: C, 45.63; H, 5.70; N, 4.84.

B. 4-(2-Aminoethoxy) benzamide (m.p. 179°–181° from ethanol; $R_f$ 0.35; methanol/chloroform, 3:7).

Analysis Calcd. for $C_9H_{12}N_2O_2$: C, 59.98; H, 6.71; N, 15.55. Found: C, 59.46; H, 6.78; N, 15.16.

Nmr and mass spectra confirmed the structures of both the products (A) and (B).

The compound, 5-(2,3-Epoxy)-propoxy-3,4-dihydrocarbostyril was prepared as follows:

Dry 5-hydroxy-3,4-dihydrocarbostyril (20.0 g., 0.122 mole); Y. Tamura et al, *Chem. Ind.*, 1435 (1970) was added with stirring to a suspension of 50% NaH dispersion (6.14 g., 0.128 mole) in dry DMF (110 ml) under $N_2$. This was followed by a portionwise addition of epichlorohydrin (33.8 g., 0.366 mole) at 30° C. After the initial reaction was over, the mixture was heated at 65° for 2 hours, stirred overnight at room temperature, filtered and the filtrate was concentrated in vacuo. When solid started to separate, the mixture was diluted with absolute ethanol and filtered to give 10.5 g. (m.p. 164°–68°) of the product which was 96% pure (TLC). The alcoholic filtrate was concentrated, the gummy residue washed several times with water, covered with ethanol and filtered to give 0.6 g. of the same material. Total yield 11.1 g. (42%). The product was identical to the one prepared by the method reported by K. Nakagawa et al, *J. Med. Chem.*, 17, 529 (1974).

EXAMPLE III

5-[2-Hydroxy-3-(3,4-Methylenedioxy-Phenethylamino]-Propoxy-3,4-Dihydrocarbostyril A mixture of equivalent amounts of 5-hydroxy-3,4-dihydrocarbostyril and 3,4-methylene dioxyphenethylamine hydrochloride (J. Org. Chem., 23, 1982 (1958) in absolute ethanol (30 ml.) containing triethylamine (2 ml.) was refluxed 5 hours. The clear solution was evaporated to dryness under reduced pressure, the pasty mass triturated with absolute ethanol, filtered and the residue collected (710 mg., positive Cl). The filtrate was acidified with ethereal HCl and evaporated to dryness. The residue was triturated with absolute ethanol and filtered. This residue (230 mg.) was combined with 710 mg. obtained earlier, dissolved in warm water and extracted with ethyl acetate. The organic extract was discarded and the aqueous layer was evaporated to dryness to give the product. Recrystallization from water gave the product melting at 242°–44° dec.

Analysis Calcd. for $C_{21}H_{24}N_2O_5$·HCl: C, 59.93; H, 5.99; N, 6.60; O, 19.00. Found: C, 59.24; H, 6.00; N, 6.80; O, 19.06.

Mass spectra of the compound was consistent with its structure.

EXAMPLE IV

The compounds produced in Examples I, II and III above were administered intravenously (i.v.) to anesthetized dogs to show their effectiveness as beta-blockers.

In the use of these compounds, they were administered in different dosages to the anesthetized dogs to determine the percent (%) inhibition of isoproterenol effect on the blood pressure and heart rate of the dogs. The compounds administered in different dosages to the anesthetized dogs are:

(I) 5-[2-hydroxy-3-(3,4-dimethoxy phenethylamino)]-propoxy-3,4-dihydrocarbostyril

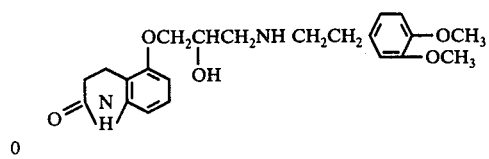

(II) 5-[2-hydroxy-3-(4-carbamoyl phenoxyethylamino)]-propoxy-3,4-dihydrocarbostyril

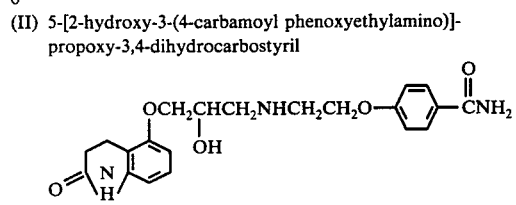

(III) 5-[2-hydroxy-3-(3,4-methylenedioxy-phenethylamino]-propoxy-3,4-dihydrocarbostyril

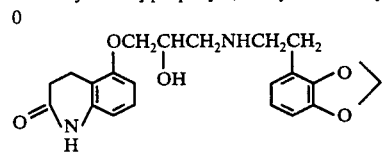

The results of the administration of the compounds are shown in the table below (BP = blood pressure; HR = heart rate):

| Compound | Dose Mg./Kg., i.v. | | Percent (%) Inhibition of Isoproternol Effect on BP and HR (Time After Administration, Minutes) | | | | |
|---|---|---|---|---|---|---|---|
| | | | 10 | 30 | 60 | 90 | 120 |
| I | 0.03 | BP | 25 | 0 | 0 | 0 | 0 |
| | | HR | 73 | 62 | 42 | 42 | 23 |
| | 0.1 | BP | 32 | 23 | 9 | 9 | 18 |
| | | HR | 65 | 43 | 35 | 22 | 19 |
| | 0.3 | BP | 68 | 48 | 56 | 12 | — |
| | | HR | 89 | 83 | 72 | 67 | — |
| II | 0.1 | BP | 56 | 44 | 17 | 44 | 22 |
| | | HR | 82 | 55 | 33 | 27 | 24 |
| | 0.3 | BP | 100 | 67 | 60 | 67 | 33 |
| | | HR | 84 | 64 | 44 | 20 | 4 |
| | 0.1 | BP | 35 | 12 | — | — | — |
| III | | HR | 55 | 24 | — | — | — |
| | 1.0 | BP | 88 | 88 | 74 | 69 | 71 |
| | | HR | 97 | 95 | 89 | 87 | 84 |

As demonstrated above, the compounds (I, II and III) are effective β-blockers. In addition, the data in the previous table also demonstrate that compound I, 5-[2-hydroxy-3-(3,4-dimethoxy phenethylamino)]-propoxy-3,4-dihydrocarbostyril, is cardioselective, indicating that it may act preferentially on the myocardium and not precipitate asthma attacks in susceptible individuals. This cardioselectivity of compound I is indicated by the results showing that as time passed by, blockade of the isoproternol blood pressure (BP) effect quickly approached zero (0) while the heart rate (HR) block lasted much longer.

We claim:

1. A compound of the formula

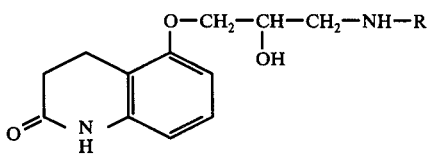

wherein R is

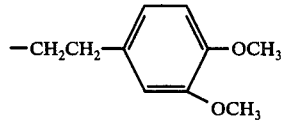

and the physiologically compatible acid addition salts thereof.

2. The compound of claim 1, 5-[2-hydroxy-3-(3,4-dimethoxy phenethylamino)]-propoxy-3,4-dihydrocarbostyril.

* * * * *